(12) United States Patent
Hogendijk (10) Patent No.: US 7,846,198 B2
(45) Date of Patent: Dec. 7, 2010

(54) VASCULAR PROSTHESIS AND METHODS OF USE

(75) Inventor: Michael Hogendijk, Palo Alto, CA (US)

(73) Assignee: NovoStent Corporation, Mountain View, CA (US)

( * ) Notice: Subject to any disclaimer, the term of this patent is extended or adjusted under 35 U.S.C. 154(b) by 789 days.

(21) Appl. No.: 10/342,427

(22) Filed: Jan. 13, 2003

(65) Prior Publication Data
US 2004/0122504 A1 Jun. 24, 2004

(51) Int. Cl.
*A61F 2/06* (2006.01)
*A61M 29/00* (2006.01)

(52) U.S. Cl. ............... 623/1.22; 623/1.15; 623/1.16; 623/1.51; 623/1.53; 606/194; 606/195; 606/198

(58) Field of Classification Search ............... 623/1.22, 623/1.15, 1.16, 1.51, 1.54, 1.53, 1.3; 606/194, 606/195, 198
See application file for complete search history.

(56) References Cited

U.S. PATENT DOCUMENTS

| | | | |
|---|---|---|---|
| 4,553,545 A | 11/1985 | Maass et al. |
| 4,655,771 A | 4/1987 | Wallsten |
| 4,665,918 A | 5/1987 | Garza et al. |
| 4,739,762 A | 4/1988 | Palmaz |
| 4,760,849 A | 8/1988 | Kropf |
| 4,768,507 A | 9/1988 | Fischell et al. |
| 4,886,062 A | 12/1989 | Wiktor |
| 4,969,458 A | 11/1990 | Wiktor |
| 5,019,090 A | 5/1991 | Pinchuk |
| 5,104,404 A | 4/1992 | Wolff |
| 5,147,370 A | 9/1992 | McNamara et al. |
| 5,246,445 A | 9/1993 | Yachia et al. |
| 5,314,444 A | 5/1994 | Gianturco |
| 5,342,387 A | 8/1994 | Summers |
| 5,344,426 A | 9/1994 | Lau et al. |
| 5,383,892 A | 1/1995 | Cardon et al. |

(Continued)

FOREIGN PATENT DOCUMENTS

EP 1 110 515 A2 6/2001

(Continued)

OTHER PUBLICATIONS

Office Action mailed Jun. 26, 2008 for U.S. Appl. No. 10/746,668, filed Dec. 23, 2003.

(Continued)

*Primary Examiner*—Vy Q. Bui
(74) *Attorney, Agent, or Firm*—James F. Hann; Haynes Beffel & Wolfeld LLP (57) ABSTRACT

The present invention is directed to an implantable vascular prosthesis configured for use in a wide range of applications, such as treating aneurysms, maintaining patency in a vessel, and allowing for the controlled delivery of therapeutic agents to a vessel wall. The prosthesis comprises a helical proximal section coupled to a distal anchoring section having a generally zig-zag configuration. The prosthesis is configured to comply to a vessel wall without substantially remodeling the vessel, and further is configured to be precisely deployed in a vessel without shifting during deployment. The prosthesis also has a substantially small delivery profile compared to other known stents, while having an increased surface area to enhance delivery of therapeutic agents.

18 Claims, 5 Drawing Sheets

U.S. PATENT DOCUMENTS

| | | | |
|---|---|---|---|
| 5,421,955 A | 6/1995 | Lau et al. | |
| 5,423,885 A | 6/1995 | Williams | |
| 5,441,515 A | 8/1995 | Khosravi et al. | |
| 5,443,500 A | 8/1995 | Sigwart | |
| 5,476,505 A | 12/1995 | Limon | |
| 5,540,713 A | 7/1996 | Schnepp-Pesch et al. | |
| 5,551,954 A | 9/1996 | Buscemi et al. | |
| 5,556,413 A | 9/1996 | Lam | |
| 5,607,445 A | 3/1997 | Summers | |
| 5,607,478 A | 3/1997 | Lentz et al. | |
| 5,707,387 A | 1/1998 | Wijay | |
| 5,716,396 A | 2/1998 | Williams, Jr. | |
| 5,741,333 A * | 4/1998 | Frid | 623/1.2 |
| 5,766,238 A | 6/1998 | Lau et al. | |
| 5,817,152 A | 10/1998 | Birdsall et al. | |
| 5,824,052 A | 10/1998 | Khosravi et al. | |
| 5,824,053 A | 10/1998 | Khosravi et al. | |
| 5,830,179 A | 11/1998 | Mikus et al. | |
| 5,833,699 A | 11/1998 | Chuter | |
| 5,837,313 A * | 11/1998 | Ding et al. | 427/2.21 |
| 5,876,432 A | 3/1999 | Lau et al. | |
| 6,027,526 A | 2/2000 | Limon et al. | |
| 6,080,191 A | 6/2000 | Summers | |
| 6,086,604 A | 7/2000 | Fischell et al. | |
| 6,156,062 A | 12/2000 | McGuiness | |
| 6,238,430 B1 | 5/2001 | Klumb et al. | |
| 6,248,122 B1 | 6/2001 | Klumb et al. | |
| 6,273,908 B1 * | 8/2001 | Ndondo-Lay | 623/1.43 |
| 6,331,189 B1 | 12/2001 | Wolinsky et al. | |
| 6,334,870 B1 | 1/2002 | Ehr et al. | |
| 6,348,065 B1 | 2/2002 | Brown et al. | |
| 6,361,556 B1 * | 3/2002 | Chuter | 623/1.11 |
| 6,409,754 B1 | 6/2002 | Smith et al. | |
| 6,423,091 B1 | 7/2002 | Hojeibane | |
| 6,425,915 B1 | 7/2002 | Khosravi et al. | |
| 6,432,128 B1 | 8/2002 | Wallace et al. | |
| 6,503,270 B1 | 1/2003 | Richter et al. | |
| 6,508,834 B1 * | 1/2003 | Pinchasik et al. | 623/1.16 |
| 6,514,285 B1 | 2/2003 | Pinchasik | |
| 6,533,805 B1 | 3/2003 | Jervis | |
| 6,540,775 B1 | 4/2003 | Fischell et al. | |
| 6,565,600 B2 * | 5/2003 | Hojeibane | 623/1.16 |
| 6,572,643 B1 | 6/2003 | Gharibadeh | |
| 6,576,006 B2 | 6/2003 | Limon et al. | |
| 6,589,276 B2 | 7/2003 | Pinchasik et al. | |
| 6,596,021 B1 | 7/2003 | Lootz | |
| 6,607,554 B2 | 8/2003 | Dang et al. | |
| 6,635,084 B2 | 10/2003 | Israel et al. | |
| 6,645,237 B2 | 11/2003 | Klumb et al. | |
| 6,656,220 B1 | 12/2003 | Gomez et al. | |
| 6,660,032 B2 | 12/2003 | Klumb et al. | |
| 6,679,911 B2 | 1/2004 | Burgermeister | |
| 6,736,844 B1 | 5/2004 | Glatt et al. | |
| 6,746,475 B1 | 6/2004 | Rivelli, Jr. | |
| 2001/0020182 A1 | 9/2001 | Klumb et al. | |
| 2002/0004676 A1 | 1/2002 | Wallace et al. | |
| 2002/0004679 A1 | 1/2002 | Eury et al. | |
| 2002/0095206 A1 | 7/2002 | Addonizio et al. | |
| 2004/0034402 A1 | 2/2004 | Bales et al. | |
| 2004/0044401 A1 | 3/2004 | Bales et al. | |
| 2004/0172123 A1 | 9/2004 | Lootz et al. | |
| 2007/0185560 A1 | 8/2007 | Roeder et al. | |

FOREIGN PATENT DOCUMENTS

| | | |
|---|---|---|
| WO | WO 97/21399 A1 | 6/1997 |
| WO | WO 98/38945 A1 | 9/1998 |
| WO | WO0062711 | 10/2000 |
| WO | WO 2006/017586 A3 | 8/2005 |

OTHER PUBLICATIONS

Amendment/Response filed on Sep. 25, 2008 in response to Jun. 26, 2008 Office Action for U.S. Appl. No. 10/746,668, filed Dec. 23, 2003.

Office Action mailed Sep. 30, 2009 for U.S. Appl. No. 10/746,668, filed Dec. 23, 2003, 5 pages.

* cited by examiner

VASCULAR PROSTHESIS AND METHODS OF USE

FIELD OF THE INVENTION

The present invention relates to an implantable vascular prosthesis configured for use in a wide range of applications, and more specifically, a prosthesis having a substantially small delivery configuration, drug delivery capabilities, and a design allowing for a precise and controlled deployment of the prosthesis.

BACKGROUND OF THE INVENTION

Today there are a wide range of intravascular prostheses on the market for use in the treatment of aneurysms, stenoses, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using an outer sheath, then self-expand when the sheath is retracted. Such stents commonly have several drawbacks, for example, the stents may experience large length changes during expansion and may shift within the vessel prior to engaging the vessel wall, resulting in improper placement. Additionally, many self-expanding stents have relatively large delivery profiles because the configuration of their struts limits further compression of the stent. Accordingly, such stents may not be suitable for use in smaller vessels, such as cerebral vessels and coronary arteries.

Other drawbacks associated with the use of coils or stents in the treatment of aneurysms is that the coils or stents, when deployed, may have a tendency to remodel or straighten a delicate cerebral vessel, which may cause further adverse consequences. Moreover, such devices may not adequately reduce blood flow from the cerebral vessel into the sac of the aneurysm, which may increase the likelihood of rupture. Generally, if a greater surface area is employed to cover the sac, the delivery profile of the device may be compromised due to the increased surface area, and the device also may be more rigid and cause remodeling of the vessel.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, then constrained within a delivery sheath. The delivery sheath is retracted to expose the distal portion of the stent and anchor the distal end of the stent. As the delivery sheath is further retracted, the subsequent individual turns of the stent unwind to conform to the diameter of the vessel wall.

The stent described in the foregoing publication has several drawbacks. For example, due to friction between the turns and the sheath, the individual turns of the stent may bunch up, or overlap with one another, when the delivery sheath is retracted. In addition, once the sheath is fully retracted, the turns may shift within the vessel prior to engaging the vessel wall, resulting in improper placement of the stent. Moreover, because the distal portion of the stent may provide insufficient engagement with the vessel wall during subsequent retraction of the remainder of the sheath, ambiguity concerning accuracy of the stent placement may arise.

When utilizing stents in interventional procedures, it may be advantageous to deliver therapeutic agents to a vessel wall via the surface of the stent. Such drug eluting stents have many advantages, such as controlled delivery of therapeutic agents over an extended period of time without the need for intervention, and reduced rates of restenosis after angioplasty procedures. Typically, the drug is disposed in the matrix of a bioabsorbable polymer coated on an exterior surface of the struts of the stents, and then gradually released into a vessel wall. The quantity of the therapeutic agent provided by the stent generally is limited by the surface area of the struts. Increasing the surface area of the struts may enhance drug delivery capability, but may compromise the overall delivery profile of the stent. There therefore exists a need for a prosthesis having a reduced delivery profile and enhanced drug delivery capabilities.

In view of these drawbacks of previously known devices, it would be desirable to provide apparatus and methods for an implantable vascular prosthesis that is configured to be used in a wide range of applications including, but not limited to, treating aneurysms, maintaining patency in a vessel, and delivering drugs to a vessel wall.

It also would be desirable to provide apparatus and methods for a vascular prosthesis that is flexible enough to conform to a natural shape of a vessel without substantially remodeling the vessel.

It further would be desirable to provide apparatus and methods for a vascular prosthesis having a distal anchoring section that allows for controlled deployment of the prosthesis at a desired location within a vessel.

It still further would be desirable to provide apparatus and methods for a vascular prosthesis that has a selectable surface area to facilitate in-vivo delivery of therapeutic agents.

It yet further would be desirable to provide apparatus and methods for a vascular prosthesis that has a substantially small delivery configuration to allow the prosthesis to be used in smaller vessels.

SUMMARY OF THE INVENTION

In view of the foregoing, it is an object of the present invention to provide apparatus and methods for an implantable vascular prosthesis that is configured to be used in a wide range of applications including, but not limited to, treating aneurysms, maintaining patency in a vessel, and delivering drugs to a vessel wall.

It is also an object of the present invention to provide apparatus and methods for a vascular prosthesis that is flexible enough to conform to a natural shape of a vessel without substantially remodeling the vessel.

It is a further object of the present invention to provide apparatus and methods for a vascular prosthesis having a distal anchoring section that allows for controlled deployment of the prosthesis at a desired location within a vessel.

It is a further object of the present invention to provide apparatus and methods for a vascular prosthesis that has a selectable surface area to facilitate in-vivo delivery of therapeutic agents.

It is yet another object of the present invention to provide apparatus and methods for a vascular prosthesis that has a substantially small delivery configuration to allow the prosthesis to be used in smaller vessels.

These and other objects of the present invention are accomplished by providing a vascular prosthesis having a contracted state and a deployed state configured to engage a vessel wall and adapt to a natural curvature of the vessel wall. The vascular prosthesis may be used in a wide range of applications, such as treating aneurysms, maintaining patency in a vessel, e.g., after an angioplasty procedure, and other procedures requiring a controlled delivery of therapeutic drugs to a vessel wall.

In a preferred embodiment, the vascular prosthesis comprises a shape memory material, such as Nitinol, and includes a distal anchoring section having a generally zig-zag configuration coupled to a proximal helical section having a helical mesh configuration formed of a plurality of turns.

The anchoring section is provided in the contracted state when constrained within an outer sheath, due to the radially inward compressive forces applied by the outer sheath. The helical section is provided in the contracted state when the plurality of turns of the helical mesh are wound down to a smaller configuration, wherein adjacent turns preferably at least partially overlap, and then are constrained within the outer sheath.

In a preferred method of operation, the proximal helical and distal anchoring sections are provided in their respective contracted states within the outer sheath and the prosthesis is fluoroscopically advanced into a selected vessel using techniques that are per se known in the art. The proximal section then is positioned adjacent a target region of a vessel, such as an aneurysm or a stenosed region. At this time, the distal section is positioned distal of the target region. The outer sheath then is retracted proximally to cause the distal section to self-deploy and engage an inner wall of the vessel distal of the target region. A distal portion of the distal section may be biased radially outward, or provided with proximally-directed teeth, to facilitate secure anchoring of the distal section within the vessel.

Once the distal section is securely anchored distal of the target region, the outer sheath further is retracted to cause the proximal section to self-deploy and engage the vessel wall at the target region. Advantageously, by providing a distal anchoring element prior to deploying the proximal section, each turn of the helical proximal section will unwind in a controlled manner as the outer sheath is retracted. This technique ensures that the prosthesis will not shift within the vessel during deployment.

The vascular prosthesis of the present invention is flexible enough to conform to the shape of a delicate vessel without substantially remodeling the vessel. In particular, the zig-zag configuration of the distal section may conform to a natural curvature of a vessel wall better than traditional stents having interconnected struts, which may be more rigid. Additionally, the helical mesh configuration of the proximal section conforms to vasculature of the target region since each of the plurality of turns are free to assume a curved configuration substantially independently of one another. Also, the proximal section of the vascular prosthesis is not compressed, as in like traditional self-expanding prostheses. Rather, the proximal section may be wound down to a contracted state and so has a substantially reduced delivery profile. This feature makes the stent of the present invention especially useful for treating defects in smaller vessels, such as cerebral arteries.

In accordance with another aspect of the present invention, the plurality of turns may comprise a substantially increased surface area relative to conventional stents that have a plurality of interconnected struts. The increased surface area of the turns is particularly advantageous for localized drug delivery. The turns may be coated with a drug-laden polymer coating or, alternatively, one or more dimples or through holes may be disposed in a lateral surface of the turns to elute drugs over an extended period of time.

Methods of using the vascular prosthesis of the present invention, for example, in the treatment of an aneurysm, also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to an implantable vascular prosthesis configured for use in a wide range of applications, such as treating aneurysms, maintaining patency in a vessel, and allowing for the controlled delivery of therapeutic agents to a vessel wall. The prosthesis has a substantially small delivery profile compared to other known devices, while having an increased surface area to allow for delivery of the therapeutic agents. Additionally, the prosthesis is configured to comply to a vessel wall without substantially remodeling the vessel, and further is configured to provide improved deployment accuracy during deployment relative to previously known devices.

Figure 1A:
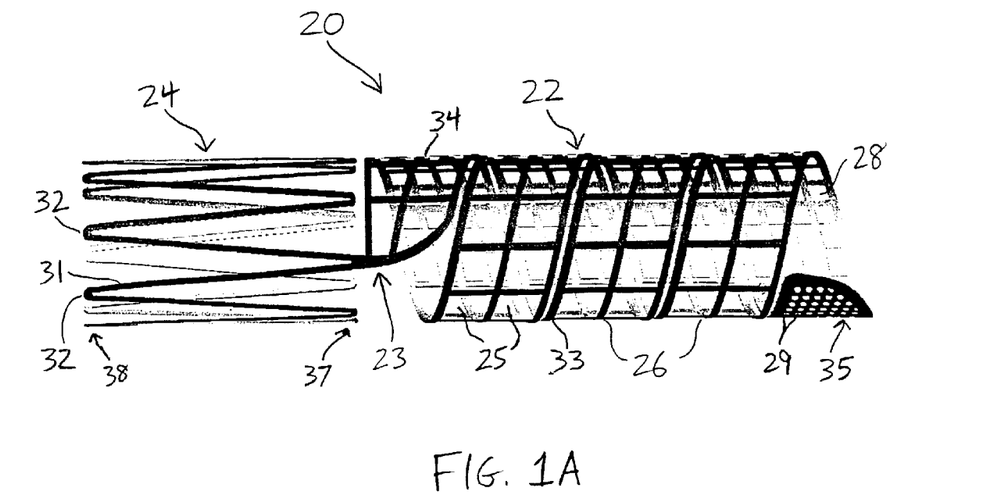
FIGS. 1A-1B are, respectively, side and perspective views of a vascular prosthesis of the present invention.
Figure 1B:
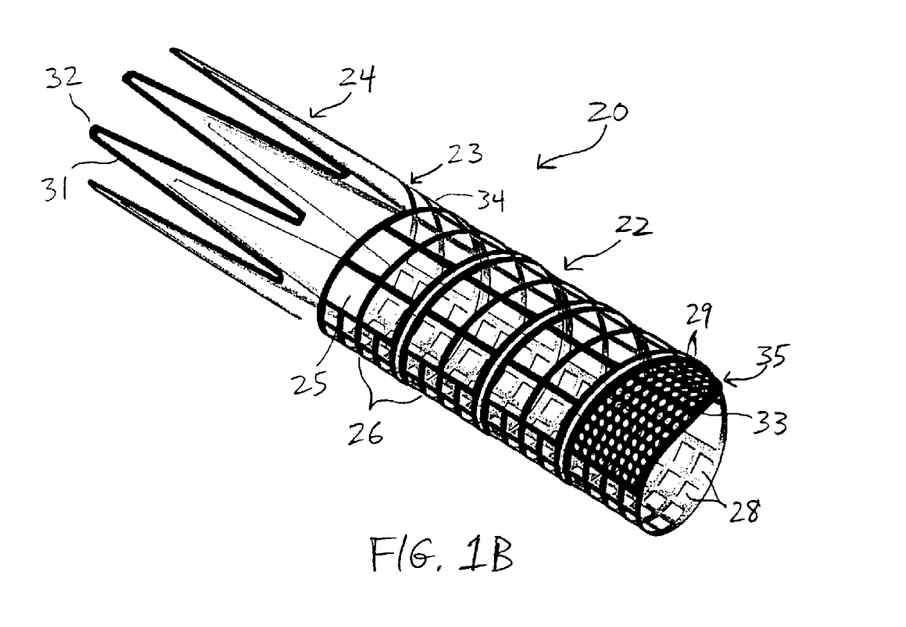

Referring now to FIG. 1, a first embodiment of a vascular prosthesis constructed in accordance with principles of the present invention is described. Vascular prosthesis 20 comprises proximal section 22 and distal section 24, each having contracted and deployed states. In FIG. 1, proximal and distal sections 22 and 24 are each depicted in their respective deployed states.

Vascular prosthesis 20 preferably is formed from a solid tubular member comprising a shape memory material, such a nickel-titanium alloy (commonly known in the art as Nitinol). The solid tubular member then is laser cut, using techniques that are per se known in the art, to a desired deployed configuration, as depicted in FIG. 1A. An appropriate heat treatment, per se known in the art, then may be applied to solid regions 33 of vascular prosthesis 20 when the device is held in the desired deployed configuration. The treatment of the shape memory material allows vascular prosthesis 20 to self-deploy to the desired deployed configuration, depicted in FIG. 1, for purposes described hereinafter.

Distal section 24 preferably has a generally zig-zag configuration in the deployed state, as shown in FIG. 1A. The zig-zag configuration preferably is formed by laser cutting a solid tube, as described hereinabove, to form a pattern comprising plurality of struts 31 disposed between plurality of bends 32.

Proximal section 22 preferably comprises a helical mesh configuration in the deployed state, as depicted in FIG. 1. The helical mesh configuration includes a plurality of substantially flat turns 26. Plurality of turns 26 may include a multiplicity of openings provided in different shapes and sizes, as illustrated by larger rectangular openings 25, smaller rectangular openings 28 and small circular openings 29. The multiplicity of openings are disposed between solid regions 33 of the shape memory material used to form vascular prosthesis 20. Alternatively, turns 26 may comprise fully covered sections 39, as depicted hereinbelow in FIG. 7C.

As will be apparent to one skilled in the art, the configuration of proximal section 22 depicted herein is merely for illustrative purposes. Any combination of covered sections 39, circular openings 29, large or small rectangular openings, or any other shape may be provided along portions of turns 26, as desired. Plurality of turns 26 similarly may comprise exclusively one type of opening, such as small circular openings 29. Alternatively, plurality of turns 26 may be completely solid, such that the openings are omitted altogether. As will be apparent to those skilled in the art, the combination of solid regions and openings may be selectively provided along the length of proximal section 22, for example, to selectively increase surface area and drug delivery capabilities along proximal section 22, or to influence flow dynamics within a vessel.

Proximal section 22 includes distal turn 34 that transitions into bend 32 of distal section 24, thereby forming junction 23. Proximal turn 35 of proximal section 22 forms a free end that permits proximal section 22 to conform to a natural configuration of a patient's vessel, as described hereinbelow with respect to FIG. 7.

Figure 2:
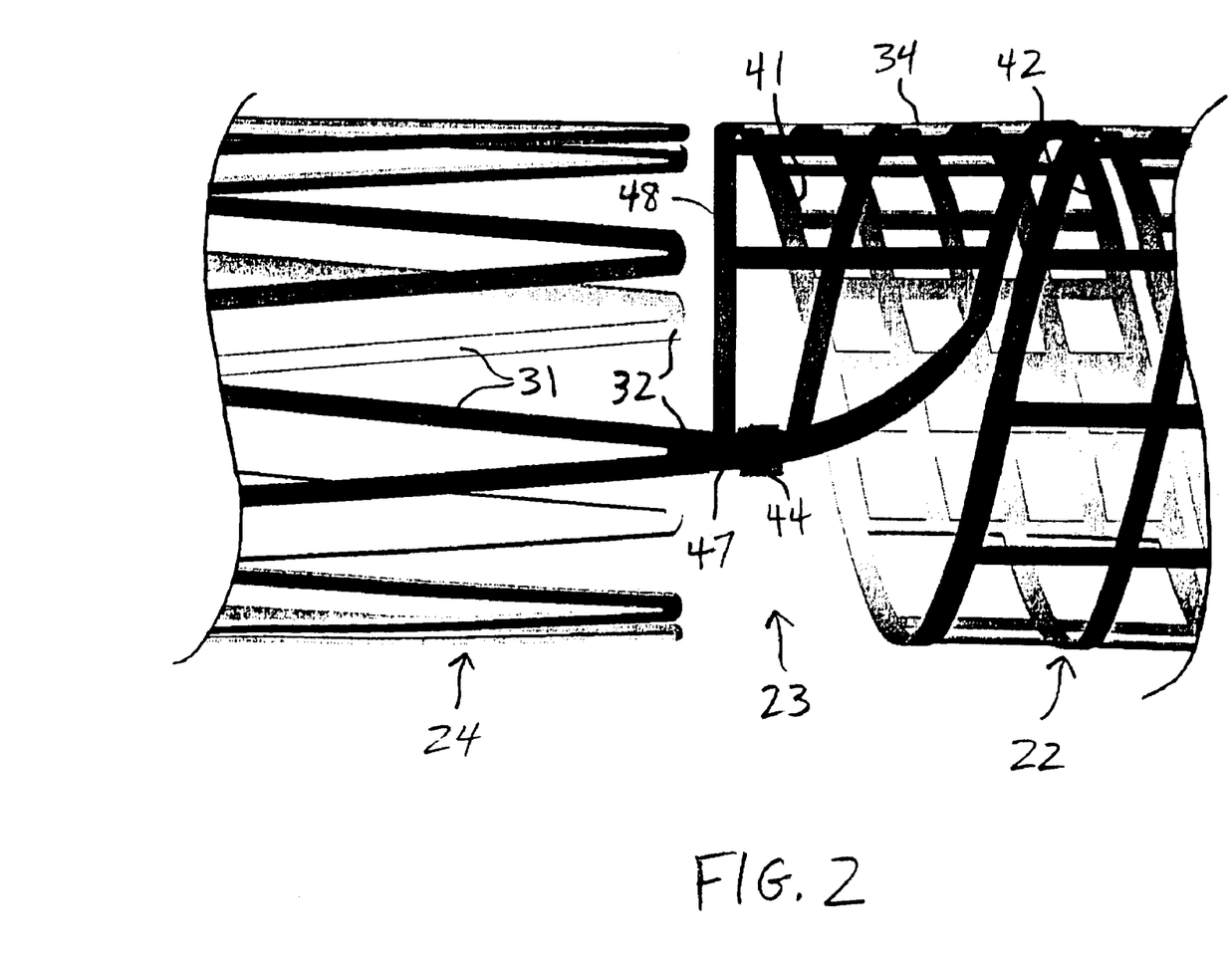
FIG. 2 is a side view describing features of the junction of the prosthesis of FIG. 1.

Referring now to FIG. 2, features of junction 23 of FIG. 1 are described in greater detail. Junction 23 is disposed between proximal and distal sections 22 and 24 of vascular prosthesis 20. Junction 23 preferably comprises extension strut 47 that is coupled to at least one bend 32 of distal section 24. Junction 23 extends in a proximal direction towards proximal section 22 and ultimately transitions into proximal wall 42 of distal turn 34, as shown in FIG. 2. The use of one extension strut 47 as in FIG. 2 permits the distal anchoring section 24 to fully expand to its deployed state before the proximal section 22 expands. See FIGS. 7A-7C.

Junction 23 further preferably comprises substantially orthogonal segment 48, i.e., a segment that is substantially orthogonal to a longitudinal axis of vascular prosthesis 20. Segment 48 transitions into extension strut 47 in the vicinity of bend 32, and further transitions into distal wall 41 of distal turn 34, as shown in FIG. 2.

Junction 23 may comprise one or more radiopaque markers 44, such as a radiopaque marker band or coating. Radiopaque marker 44 facilitates positioning of junction 23 at a desired longitudinal position within a patient's vessel, and further facilitates alignment of vascular prosthesis 20 at a desired radial orientation within the vessel. For example, radiopaque marker 44 may be used to orient proximal section 22 so that a desired lateral surface of proximal section 22, e.g., comprising covered sections 39 or small circular openings 29, deploys to overlay the arc of a vessel in which an aneurysm is situated.

It will be apparent to those skilled in the art that junction 32 may comprise other strut arrangements to connect distal section 24 to proximal section 22. For example, more than one extension struts 47 may be coupled between bends 32 and distal turn 34 of proximal section 22. Alternatively, proximal and distal sections 22 and 24 may be manufactured as two distinct sections, then coupled together to form a junction. In this embodiment, the junction may be formed when distal turn 34 of proximal section 22 is coupled to one or more bends 32 situated at proximal end 37 of distal section 24. Distal turn 34 may be coupled to one or more bends 32 using a means for bonding, such as a solder, or the sections alternatively may be mechanically coupled together, for example, using a rivet or any other means, as will be apparent to one skilled in the art.

Figures 3, 4, 5:
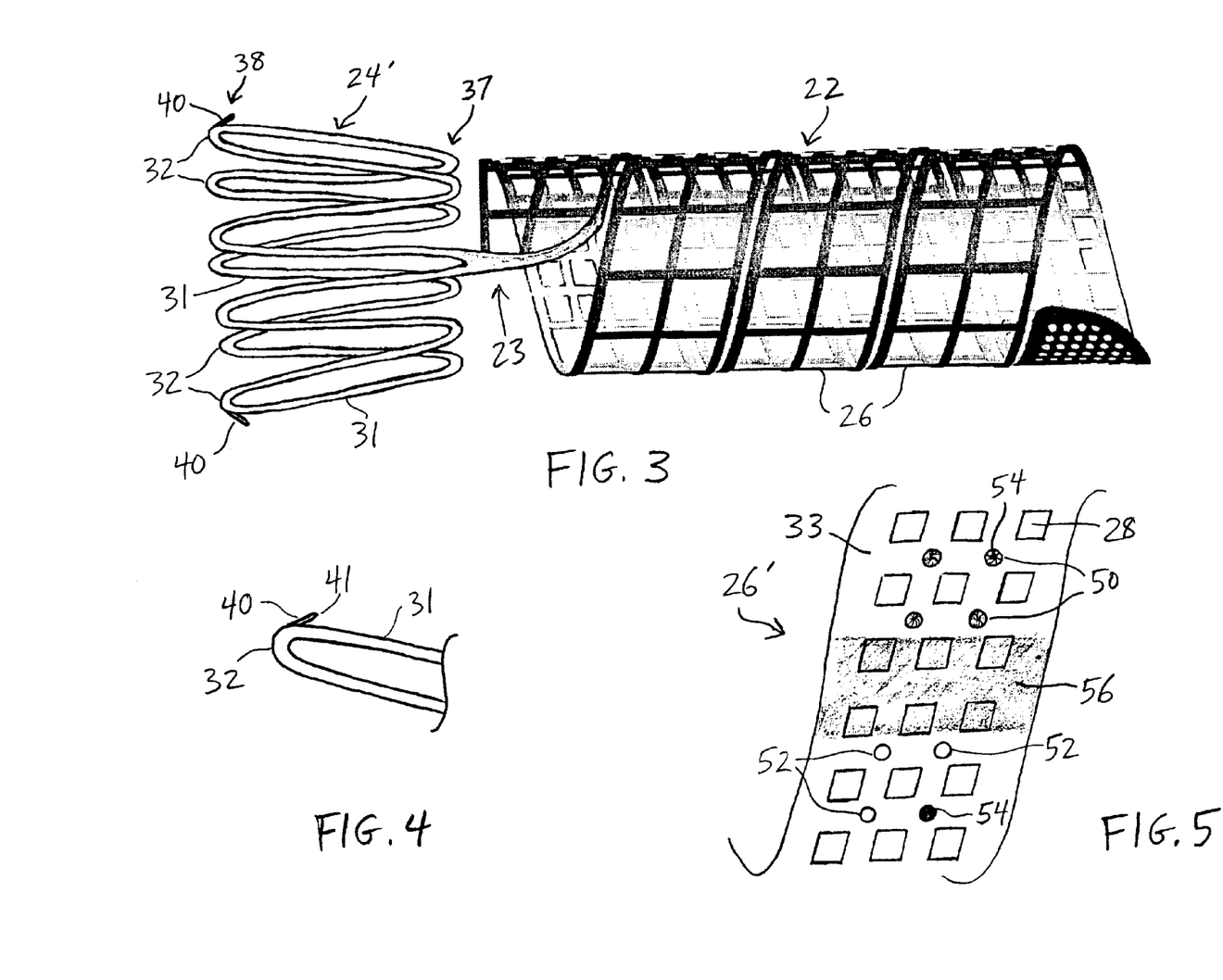
FIG. 3 is a side view of a vascular prosthesis having a distal section that is biased radially outward.
FIG. 4 is an enlarged view of the distal end of the prosthesis of FIG. 3.
FIGS. 5 is a side view illustrating different drug delivery modalities.

Referring now to FIG. 3, an alternative embodiment of distal section 24 of FIG. 1 is described. In FIG. 3, alternative distal section 24' has proximal end 37 and distal end 38. Distal end 38 is biased radially outward with respect to the longitudinal axis of vascular prosthesis 20. The deployed configuration of alternative distal section 24' may be established by heat treating a shape memory material, using techniques that are per se known in the art, as described above. Alternative distal section 24' is configured to impose an increased radial outward force upon a patient's vessel and may further improve anchoring of the prosthesis within the vessel.

Distal end 38 of alternative distal section 24' further may comprise at least one tooth 40 protruding from bend 32 and/or a distal portion of strut 31, as depicted in FIG. 4. Tooth 40 is configured to extend radially outward and in a proximal direction with respect to a longitudinal axis of vascular prosthesis 20. Each tooth 40 may comprise sharpened tip 41, which is configured to engage a patient's vessel when alternative distal section 24' is deployed in a vessel, as described in hereinbelow with respect to FIG. 7.

Referring now to FIG. 5, different drug delivery modalities that may be used in conjunction with vascular prosthesis 20 of the present invention are described. In FIG. 5, illustrative turn 26' of proximal section 22 comprises multiplicity of openings 28 disposed between solid regions 33, and further comprises at least one dimple 50 and/or through hole 52 disposed in solid regions 33. Each dimple 50 and through hole 52 may have therapeutic agent 54 disposed therein. Therapeutic agent 54 may be disposed in the matrix of a bioabsorbable polymer, and the drug may be gradually released into a localized region of an arterial wall. Dimples 50 may be selectively disposed on an interior surface of turn 26', and/or disposed on an exterior surface of turn 26', as depicted in FIG. 5.

One or more turns 26 may be selectively coated with elastomeric polymer 56, such as polyurethane. Elastomeric polymer 56 may partially or fully cover selected regions of turns 26. For example, elastomeric polymer 56 may be disposed on one arc of the circumference of proximal section 22 to overlay an aneurysm and reduce blood flow into a sac of the aneurysm. Additionally, therapeutic agent 54 may be disposed on elastomeric polymer 56, which increases the working surface area of proximal section 22. Alternatively, the therapeutic agent may be disposed directly on solid region 33, either with or without the use of elastomeric polymer 56.

Figure 6:
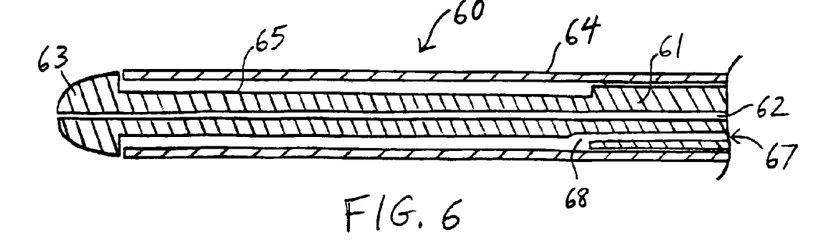
FIGS. 6 is a side sectional view of a delivery system that may be used in conjunction with the vascular prosthesis of FIG. 1.

Referring now to FIG. 6, a delivery system suitable for use with the vascular prosthesis of the present invention is described. In FIG. 6, delivery system 60 is similar to that disclosed in U.S. Pat. No. 4,665,918 to Garza et al., and includes catheter 61 having central lumen 62, nose cone 63 and outer sheath 64. Catheter 61 includes recessed portion 65 that cooperates with outer sheath 64 to retain proximal and distal sections 22 and 24 of vascular prosthesis 20 in their respective contracted states for transluminal delivery.

Delivery system 60 also may comprise fluid delivery lumen 67, which may be used to deliver chilled saline to vascular prosthesis 20 during delivery of the device. Fluid delivery lumen 67 may be disposed within catheter 61, as depicted in FIG. 6, and one or more ports 68 may be formed in a distal lateral surface of catheter 61 to facilitate fluid communication between lumen 67 and recessed portion 65.

Figure 7A:
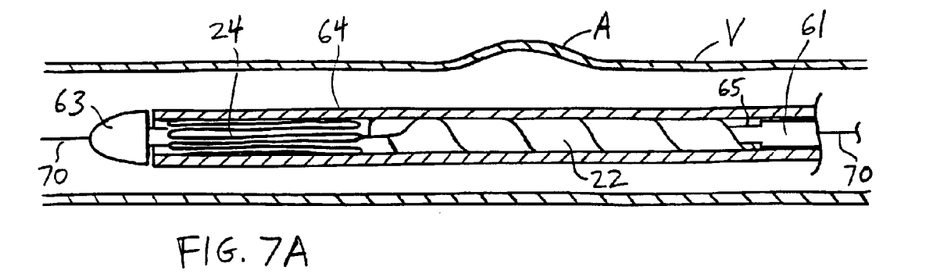
FIGS. 7A-7C are side sectional views illustrating use of the vascular prosthesis of FIG. 1 in the treatment of an aneurysm.
Figure 7B:
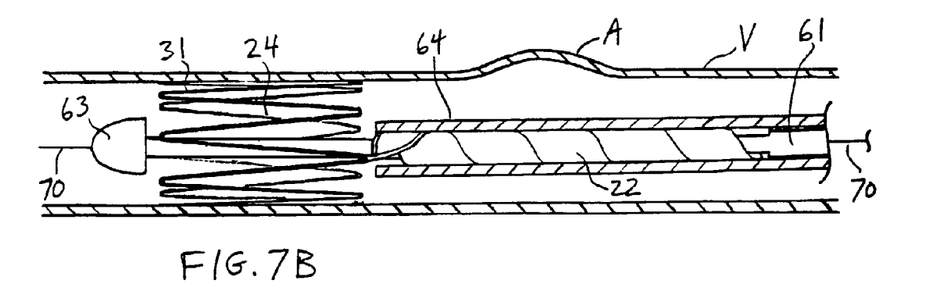
Figure 7C:
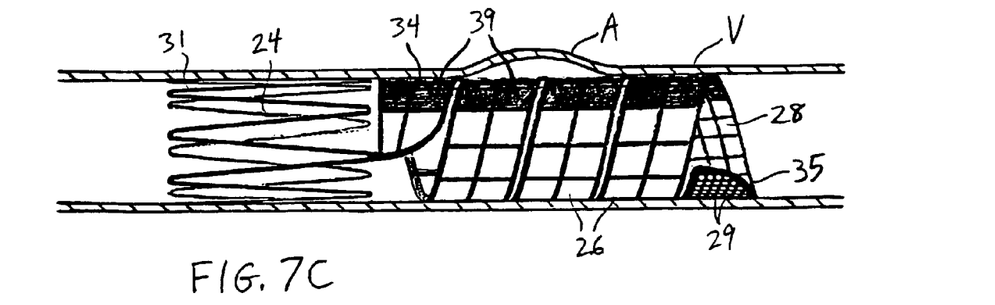

Referring now to FIG. 7, preferred method steps of using vascular prosthesis 20 of the present invention, for example, in the treatment of an aneurysm, is described. It will be apparent from the method steps described herein that vascular prosthesis 20 also may be used in general stenting procedures, for example, to maintain patency in a vessel after an angioplasty procedure, or may be used as an intravascular drug delivery device, or may be used in other applications apparent to those skilled in the art.

Referring now to FIG. 7A, vascular prosthesis 20 of FIG. 1 is provided in the fully contracted state disposed between recessed portion 65 of catheter 61 and outer sheath 64 of FIG. 6. Specifically, distal section 24 is compressed to its contracted delivery state about recessed portion 65 of catheter 61, and the plurality of turns of proximal section 22 are wound down to a contracted delivery state about recessed portion 65, as shown in FIG. 7A. Outer sheath 64 is disposed over proximal and distal sections 22 and 24, as depicted, to retain both sections in their contracted states.

First, guide wire 70 is percutaneously and transluminally advanced through a patient's vasculature, using techniques that are per se known in the art, until a distal end of guide wire 70 is positioned distal of aneurysm A, which is situated in vessel V. Delivery system 60, having vascular prosthesis 20 contracted therein, then is advanced over guide wire 70 via central lumen 62 of catheter 61. Nose cone 63 serves as an atraumatic bumper during advancement of delivery system 60. Delivery system 60 is advanced under fluoroscopic guidance until proximal section 22 is situated adjacent aneurysm A, as shown in FIG. 7A.

During advancement of delivery system 60 though a patient's vasculature, chilled saline preferably is delivered to vascular prosthesis 20 via fluid delivery lumen 67 and port 68. The chilled saline may be used to increase the flexibility of prosthesis 20 to facilitate advancement of delivery system 60 over guide wire 70.

In a next step, outer sheath 64 is retracted proximally to cause distal section 24 to self-deploy distal of aneurysm A, as shown in FIG. 7B. Struts 31 of distal section 24 expand in a radial direction to engage an inner wall of vessel V. Hooks 40 of FIG. 3 may engage vessel V, and/or the distal end of distal section 24 may be biased radially outward with respect to the proximal end (see FIG. 3) to enhance the engagement between distal section 24 and the vessel wall.

With distal section 24 anchored distal of aneurysm A, outer sheath 64 then is further retracted proximally to cause distal turn 34 of proximal section 22 to unwind and deploy to its predetermined shape, as shown in FIG. 7C. As the outer sheath is further retracted, each subsequent turn 26 unwinds one at a time and engages and conforms to an inner wall of vessel V in a controlled manner. When prosthesis system 20 is fully deployed, delivery system 60 then is proximally retracted over guide wire 70 and withdrawn from the patient's vessel, and guide wire 70 then is removed.

In accordance with one aspect of the present invention, deploying distal section 24 prior to deploying proximal section 22 allows distal section 24 to serve as an anchoring mechanism that allows for a controlled deployment of the helical turns of proximal section 22. Advantageously, turns 26 of proximal section 22 will be accurately deployed within vessel V, with substantially no proximal or distal shifting with respect to the vessel as outer sheath 64 is retracted.

Moreover, by deploying distal section 24 prior to deploying proximal section 22, drawbacks associated with the device described in the above-referenced publication to Rivelli may be overcome. Specifically, without a distal anchoring element, the multiplicity of turns of the stent described in the Rivelli publication may experience a tendency to "bunch up," i.e., overlay one another, as the outer sheath is retracted due to friction between the turns and the outer sheath. In the present invention, distal section 24 serves as an anchoring mechanism prior to retraction of the outer sheath over the proximal section. Accordingly, such a distal anchoring mechanism overcomes potential friction and turns 26 will be less inclined to bunch up.

In accordance with another aspect of the present invention, vascular prosthesis 20 of the present invention is configured to be flexible enough to substantially conform to the shape of vessel V without causing the vessel to remodel. In particular, the zig-zag configuration of distal section 24 and the helical configuration of proximal section 22 allow for increased flexibility of prosthesis 20. The pitch associated with plurality of turns 26 may be varied to vary the overall flexibility of proximal section 22. A lower pitch, whereby adjacent turns 26 are spaced relatively close together, may be employed to increase flexibility of proximal section 22. A lower pitch is desirable, for example, to treat cerebral aneurysms so that turns 26 may conform to the vasculature without causing remodeling of the vessel. Conversely, a higher pitch, whereby adjacent turns 26 are spaced further apart, may be employed to increase the rigidity of proximal section 22. Such a design may be desirable for use in maintaining patency in a stenosed vessel by increasing rigidity of proximal section 22. As a yet further embodiment, the width of the coil may be tapered, as described in the Rivelli publication.

In accordance with another aspect of the present invention, covered sections 39 may be positioned to overlay aneurysm A to significantly reduce blood flow into aneurysm A. Alternatively, smaller rectangular openings 28 or small circular openings 29 may overlay aneurysm A to reduce blood flow into the sac of the aneurysm. Over time, the intima of vessel V will grow over plurality of turns 26 of proximal section 22 to completely exclude the aneurysm A from vessel V.

As noted hereinabove, the configuration of proximal section 22 depicted in FIG. 7C is merely for illustrative purposes. Any combination of covered sections 39, circular openings 29, large or small rectangular openings, or any other shape may be provided along turns 26, as desired. Plurality of turns 26 similarly may exclusively comprise one type of opening, e.g., small circular openings 29. Alternatively, plurality of turns 26 may be completely solid such that the openings are omitted altogether.

In accordance with yet another aspect of the present invention, therapeutic agents may be delivered to expedite treatment of the aneurysm or prevent restenosis. As described hereinabove with respect to FIG. 5, therapeutic agent 54 may be delivered to a desired location within vessel V, either using internal or external dimples 50, through holes 52, elastomeric polymer 56 and/or solid regions 33 of one or more turns 26.

Therapeutic agent 54 may include, for example, antiplatelet drugs, anticoagulant drugs, agents used for purposes of providing gene therapy to a target region, or any other agent, and may be tailored for a particular application. Radiopaque markers (not shown) may be selectively disposed on turns 26 in the vicinity of the therapeutic agents to facilitate alignment of the therapeutic agents with a target site of a vessel wall. Advantageously, higher doses of such agents may be provided using vascular prosthesis 20 of the present invention, relative to previously known coils or stents having interconnected struts, due to the increased surface area associated with turns 26.

Figure 8A:
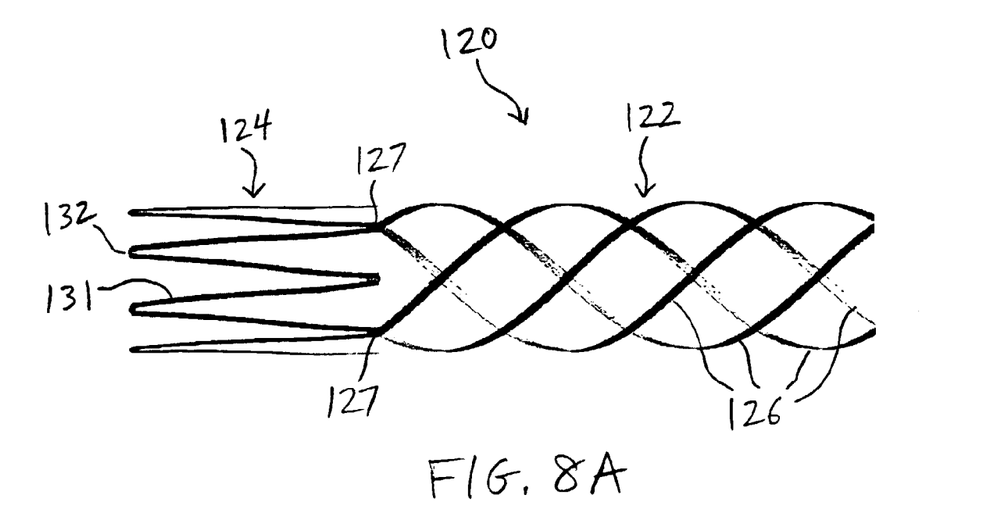
FIGS. 8A-8B are an alternative embodiment of the vascular prosthesis of the present invention.
Figure 8B:
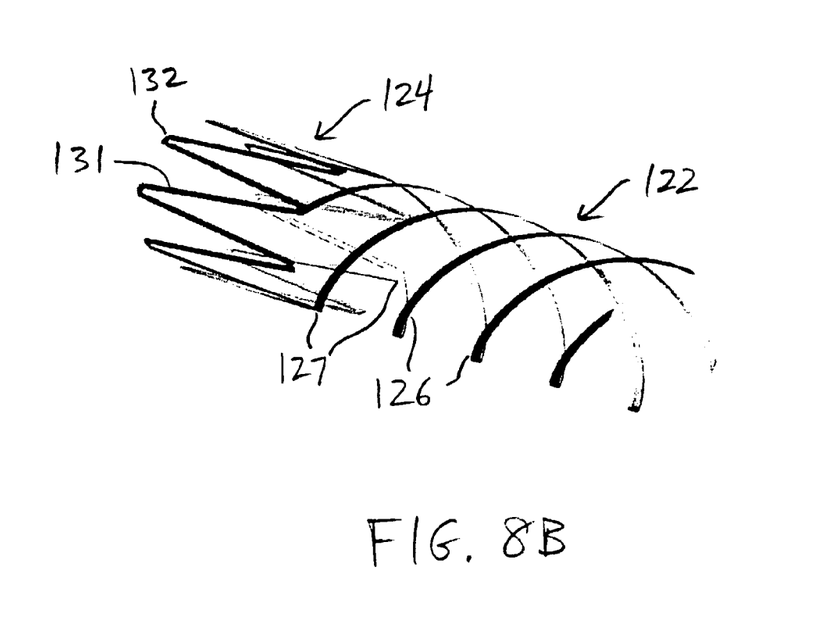

Referring now to FIG. 8, an alternative embodiment of the vascular prosthesis of the present invention is described. Vascular prosthesis 120 comprises proximal section 122 and distal sections 124. Distal section 124 preferably is provided in accordance with distal section 24 of FIG. 1 and comprises a generally zig-zag configuration including struts 131 and bends 132.

Proximal section 122 includes a plurality of individual helical turns 126. Each turn has a distal end that is coupled to a respective bend 132 of distal section 124 at junctions 127, as shown in FIG. 8. Individual helical turns 126 are aligned in a pattern such that each turn maintains its own helical curvature without overlapping with an adjacent turn, as depicted in FIG. 8. Individual helical turns 126 of vascular prosthesis 120 may be heat treated to self-deploy to the configuration shown, and may be wound down to a small diameter in which turns 126 are constrained within delivery system 60 of FIG. 6. The deployment of vascular prosthesis 120 is substantially similar to the deployment of prosthesis 20, as described in detail hereinabove with respect to FIGS. 7, and vascular prosthesis 120 encompasses many of the advantages noted hereinabove with respect to vascular prosthesis 20.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. A vascular prosthesis for implantation in a body vessel, the vascular prosthesis comprising:
    a circumferentially non-expanding, unwindingly radially self-expanding helical section having distal and proximal ends and comprising a coil-shaped helical element extending more than 360° about a longitudinal axis of the prosthesis;
    a circumferentially radially self-expanding anchoring section joined to either the distal end or the proximal end;
    the anchoring section comprising a circumferentially continuous tubular section having a plurality of circumferentially radially expandable elements connected to one another;
    the helical and anchoring sections being self-expandable from a contracted state, suitable for transluminal insertion into a body vessel, to an expanded, deployed state, for engagement with the vessel wall;
    the helical section being joined to the anchoring section at a junction, the junction consisting of one extension strut connecting the anchoring section and the helical section whereby the anchoring section can fully expand to the expanded, deployed state before the helical section expands; and
    said helical element comprising a plurality of turns, adjacent ones of said plurality of turns at least partially overlap when in the contracted state.

2. The vascular prosthesis of claim 1 wherein the helical section and the anchoring section each comprise a shape memory material.

3. The vascular prosthesis of claim 2 wherein the shape memory material is a nickel titanium alloy.

4. The vascular prosthesis of claim 1 wherein the circumferentially radially expandable elements comprise a plurality of elongate struts having a generally zig-zag configuration when in the contracted state.

5. The vascular prosthesis of claim 1 wherein the helical portion comprises inner and outer surfaces and edges joining the inner and outer surfaces, and further comprising openings disposed in the outer surface.

6. The vascular prosthesis of claim 5 wherein the openings comprise at least one of a circular configuration or a rectangular configuration.

7. The vascular prosthesis of claim 5 further comprising an elastomeric polymer disposed on a portion of the outer surface.

8. The vascular prosthesis of claim 5, wherein at least one of the openings comprises a dimple configured to house a therapeutic agent.

9. The vascular prosthesis of claim 5, wherein at least one of the openings comprises a through-hole configured to house a therapeutic agent.

10. The vascular prosthesis of claim 1 wherein a portion of at least one of the plurality of turns comprises a covered region.

11. The vascular prosthesis of claim 1 wherein the anchoring section has a proximal end and a distal end, the distal end configured to be biased radially outward with respect to the proximal end in the deployed state.

12. The vascular prosthesis of claim 11 wherein the distal end of the anchoring section comprises at least one tooth extending radially outward and in a proximal direction.

13. The vascular prosthesis of claim 1 wherein the junction comprises a radiopaque marker.

14. The vascular prosthesis of claim 1 wherein the plurality of turns have a pitch selected responsive to characteristics of the body vessel.

15. The vascular prosthesis of claim 1 further comprising sets of coil-shaped helical portions having generally parallel helical turns.

16. The vascular prosthesis of claim 1 further comprising a pitch associated with the plurality of turns, wherein the pitch is configured to be varied for different applications.

17. The vascular prosthesis of claim 1 wherein the width of the plurality of turns varies along the length of the prosthesis.

18. The vascular prosthesis of claim 1 wherein the helical element extends more than 720° about the longitudinal axis.

* * * * *